(12) United States Patent
Schaffer et al.

(10) Patent No.: US 6,451,970 B1
(45) Date of Patent: Sep. 17, 2002

(54) PEPTIDE DERIVATIVES

(75) Inventors: Lauge Schaffer, Copenhagen; Per Balschmidt, Espergaerde, both of (DK)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/801,393

(22) Filed: Feb. 20, 1997

(30) Foreign Application Priority Data

Feb. 21, 1996 (DK) ................................ 0188/96

(51) Int. Cl.⁷ ................................ A61K 38/28
(52) U.S. Cl. .......................... 530/303; 514/3
(58) Field of Search ................ 530/303; 514/3

(56) References Cited

U.S. PATENT DOCUMENTS

| | | | |
|---|---|---|---|
| 3,869,437 A | * 3/1975 | Lindsay et al. | 260/112.7 |
| 4,608,364 A | 8/1986 | Grau | |
| 5,336,782 A | 8/1994 | Ebashi et al. | |
| 5,361,347 A | * 11/1994 | Baker et al. | 530/303 |
| 5,414,089 A | 5/1995 | Ebashi et al. | |
| 5,646,242 A | * 7/1997 | Baker et al. | 530/303 |

FOREIGN PATENT DOCUMENTS

| | | | |
|---|---|---|---|
| EP | 511600 | * | 11/1992 |
| WO | WO 94/07519 | | 4/1994 |
| WO | 07931 | * | 3/1995 |
| WO | WO 95/07931 | | 3/1995 |
| WO | WO 95/17423 | | 6/1995 |
| WO | WO 96/15148 | | 5/1996 |
| WO | WO 96/22997 | | 8/1996 |
| WO | WO 96/29344 | | 9/1996 |
| WO | WO 97/31022 | | 8/1997 |

OTHER PUBLICATIONS

Havelund S. et al. Diabetologia, 38, Suppl. 1, A192, Jan. 1995.*
Kurtzhals et al. J. Pharm. Sci. 85(3), 304–8, Mar. 1996.*
Patent Abst. of Japan 14(7), C–673 JP, A, 63–83912 (Kodama k.k.) Oct. 11, 1989.

* cited by examiner

Primary Examiner—William N. Phillips
(74) Attorney, Agent, or Firm—Reza Green, Esq.; Richard W. Bork, Esq.

(57) ABSTRACT

The present invention relates to derivatives of insulin and insulin analogues wherein the N-terminal amino group of the B-chain and/or the $\epsilon$-amino group of Lys in position B28, B29 or B30 has a substituent of the formula —CO—W—COOH wherein W is a divalent long chain hydrocarbon group having from 12 to 22 carbon atoms and zinc complexes thereof are soluble at physiological pH values and exhibit a long disappearance half-life from the injection site after subcutaneous injection.

4 Claims, No Drawings

PEPTIDE DERIVATIVES

CROSS-REFERENCE TO RELATED APPLICATIONS

This application claims priority of Danish application 0188/96 filed Feb. 21, 1996, the contents of which is fully incorporated herein by reference.

FIELD OF THE INVENTION

The present invention relates to novel derivatives of naturally occurring insulins and analogues thereof which derivatives are soluble and have a protracted profile of action, to methods of providing such derivatives, to pharmaceutical compositions containing them and to the use of such derivatives in the treatment of diabetes.

BACKGROUND OF THE INVENTION

Many diabetic patients are treated with multiple daily insulin injections in a regimen comprising one or two daily injections of a protracted insulin to cover the basal requirement supplemented by bolus injections of a rapid acting insulin to cover the requirement related to meals.

Protracted insulin compositions are well known in the art. Thus, one main type of protracted insulin compositions comprises injectable aqueous suspensions of insulin crystals or amorphous insulin. In these compositions, the insulin compounds utilized typically are protamine insulin, zinc insulin or protamine zinc insulin.

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the storage of insulin suspensions, the temperature must be kept within more narrow limits than for insulin solutions in order to avoid lump formation or coagulation.

While it was earlier believed that protamines were non-immunogenic, it has now turned out that protamines can be immunogenic in man and that their use for medical purposes may lead to formation of antibodies (Samuel et al., Studies on the immunogenicity of protamines in humans and experimental animals by means of a micro-complement fixation test, Clin. Exp. Immunol. 33, pp. 252–260 (1978)).

Also, evidence has been found that the protamine-insulin complex is itself immunogenic (Kurtz et al., Circulating IgG antibody to protamine in patients treated with protamine-insulins. Diabetologica 25, pp. 322–324 (1983)). Therefore, with some patients the use of protracted insulin compositions containing protamines must be avoided.

Another type of protracted insulin compositions are solutions having a pH value below physiological pH from which the insulin will precipitate because of the rise in the pH value when the solution is injected. A drawback is that the solid particles of the insulin act as a local irritant causing inflammation of the tissue at the site of injection.

WO 91/12817 (Novo Nordisk A/S) discloses protracted, soluble insulin compositions comprising insulin complexes of cobalt (III). The protraction of these complexes is only intermediate and the bioavailability is reduced.

Human insulin has three primary amino groups: the N-terminal group of the A-chain and of the B-chain and the ε-amino group of $LysB^{29}$. Several insulin derivatives which are substituted in one or more of these groups are known in the prior art. Thus, U.S. Pat. No. 3,528,960 (Eli Lilly) relates to N-carboxyaroyl insulins in which one, two or three primary amino groups of the insulin molecule has a carboxyaroyl group. No specifically $N^{\epsilon B29}$-substituted insulins are disclosed.

According to GB Patent No. 1,492,997 (Nat. Res. Dev. Corp.), it has been found that insulin with a carbamyl substitution at $N^{\epsilon B29}$ has an improved profile of hypoglycaemic effect.

JP laid-open patent application No. 1-254699 (Kodama Co., Ltd.) discloses insulin wherein an alkanoyl group is bound to the amino group of $Phe^{B1}$ or to the ε-amino group of $Lys^{B29}$ or to both of these. The stated purpose of the derivatisation is to obtain a pharmacologically acceptable, stable insulin preparation.

Insulin analogues, which in the B30 position have an amino acid having at least five carbon atoms which cannot necessarily be coded for by a triplet of nucleotides, are described in JP laid-open patent application No. 57-067548 (Shionogi). The insulin analogues are claimed to be useful in the treatment of diabetes mellitus, particularly in patients who are insulin resistant due to generation of bovine or swine insulin antibodies.

U.S. Pat. No. 5,359,030 (Ekwuribe, Protein Delivery, Inc.) describes conjugation-stabilized polypeptide compositions for oral or parenteral administration comprising a polypeptide covalently coupled with a polymer including a linear polyalkylene moiety and a lipophilic moiety, said moieties being arranged so relative to each other that the polypeptide has an enhanced in vivo resistance to enzymatic degradation.

EP 511600 A2 relates i.a. to protein derivatives of the formula [protein][Z]$_n$ wherein [protein] represents a protein having n amino residues each derivable from an amino group by removal of one of its hydrogen atoms, instead of amino groups, [Z] is a residue represented by the formula —CO—W—COOH wherein W is a divalent long chain hydrocarbon group which may also contain certain hetero atoms and n represents an average of the number of amide bonds between [Z] and [protein]. It is mentioned that the protein derivatives of the invention have an extremely prolonged serum half-life as compared with the proteins from which they are derived and that they exhibit no antigenicity. It is also mentioned, that insulin is one of the proteins from which derivatives according to the invention can be made, but no specific insulin derivatives are disclosed in EP 511600 nor is there any indication of a preferred [Z] or (a) preferred position(s) in which [Z] should be introduced in order to obtain useful insulin derivatives.

WO 95/07931 (Novo Nordisk A/S) discloses insulin derivatives in which the amino acid at position B30 is (a) a non-codable lipophilic amino acid having from 10 to 24 carbon atoms in which case the ε-amino group of $Lys^{b29}$ has a lower acyl substituent or (b) any codable amino acid, in which case the ε-amino group of $LysB^{29}$ has a lipophilic substituent or (c) deleted, in which case the ε-amino group of $Lys^{B29}$ has a lipophilic substituent. The insulin derivatives are soluble at physiological pH values and have a protracted profile of action.

By "insulin derivative" as used herein is meant a peptide having a molecular structure similar to that of human insulin including the disulphide bridges between $Cys^{A7}$ and $Cys^{B7}$ and between $Cys^{A20}$ and $Cys^{B19}$ and an internal disulphide bridge between $Cys^{A6}$ and $Cys^{A11}$, and which has insulin activity. When the amino acid at position B1 is deleted, the position of the remaining amino acids of the B-chain are not renumbered.

Despite the many improvements already made in the field there still is a need for novel protracted injectable insulin compositions which are solutions and contain insulins which stay in solution after injection and possess minimal inflammatory and immunogenic properties.

One object of the present invention is to provide insulin derivatives soluble at physiological pH values and having a protracted profile of action.

Another object of the present invention is to provide insulin derivatives which have a long disappearance half-life from the injection site after subcutaneous injection.

A further object of the present invention is to provide a pharmaceutical composition comprising the insulin derivatives according to the invention.

A still further object of the invention is to provide a non-immunogenic insulin derivative.

A still further object of the invention is to provide a method of making the insulin derivatives of the invention.

A still further object of the invention is to provide a method of treating diabetes.

SUMMARY OF THE INVENTION

Surprisingly, it has turned out that certain derivatives of naturally occurring insulins and insulin analogues wherein the amino group of the N-terminal amino acid of the B-chain and/or the ε-amino group of $Lys^{B29}$ has a lipophilic substituent of the formula —CO—W—COOH as defined below have a protracted profile of action and are soluble at physiological pH values.

Accordingly, in its broadest aspect, the present invention relates to an insulin derivative as shown in formula I:

Formula I

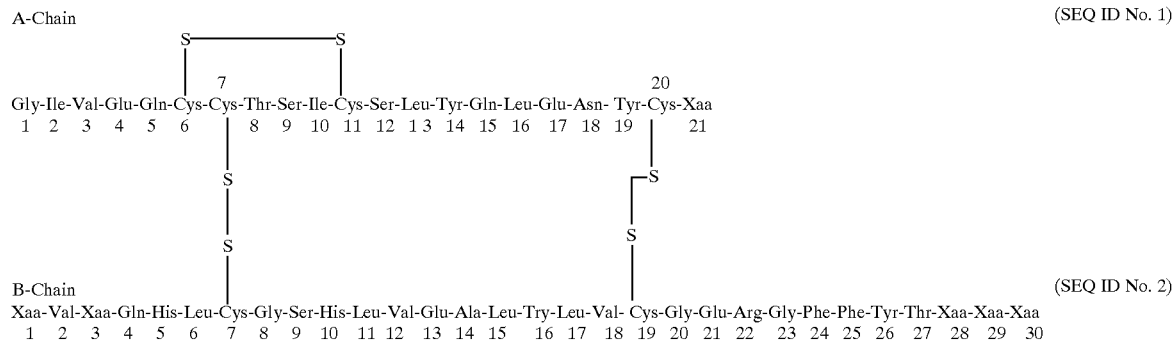

(SEQ ID No. 1)

(SEQ ID No. 2)

wherein
  Xaa at positions A21 and B3 are, independently, any amino acid residue which can be coded for by the genetic code except Lys, Arg and Cys;
  Xaa at position B1 is (a) Phe, which is optionally substituted in the amino group with a substituent of the formula —CO—W—COOH wherein W is a divalent long chain hydrocarbon group having from 12 to 22 carbon atoms; or (b) deleted, in which case the amino group of Val at position B2 is either free or has a substituent of the formula —CO—W—COOH as defined above;
  Xaa at position B28 is (a) Pro, in which case Xaa at position B29 is Lys which optionally, in its ε-amino group, has a substituent of the formula —CO—W—COOH as defined above; (b) Ser, in which case Xaa at position B29 is Lys which optionally, in its ε-amino group, has a substituent of the formula —CO—W—COOH as defined above; or (c) Lys which optionally, in its ε-amino group, has a substituent of the formula —CO—W—COOH as defined above, in which case, whether the ε-amino group of the Lys has the optional substituent or not, Xaa at position B29 is Pro;
  Xaa at position B30 is (a) Thr; (b) Ala; or (c) deleted; and any zinc complexes thereof, with the proviso that the insulin derivative of formula I has at least one lipophilic substituent of the formula —CO—W—COOH as defined above.

In another aspect, the invention relates to an insulin derivative of the general formula I above wherein Xaa at position A21, B1 and B3 are as defined above, while Xaa at position B28 is Asp, Xaa at position B29 is Lys which, in its ε-amino group, has a substituent of the formula —CO—W—COOH as defined above and Xaa at position B30 is Thr.

In another aspect, the invention relates to an insulin derivative of the general formula I above wherein Xaa at position A21, B1 and B3 are as defined above, while Xaa at position B28 is Pro, Xaa at position B29 is Thr and Xaa at position B30 is Lys which, in its ε-amino group, has a substituent of the formula —CO—W—COOH as defined above and.

In one preferred embodiment of the invention, the divalent long chain hydrocarbon group, W, is $—(CH_2)_{12}—$.

In another preferred embodiment of the invention, the divalent long chain hydrocarbon group, W, is $—(CH_2)_{13}—$.

In another preferred embodiment of the invention, the divalent long chain hydrocarbon group, W, is $—(CH_2)_{14}—$.

In another preferred embodiment of the invention, the divalent long chain hydrocarbon group, W, is $—(CH_2)_{15}—$.

In another preferred embodiment of the invention, the divalent long chain hydrocarbon group, W, is $—(CH_2)_{16}—$.

In another preferred embodiment of the invention, the divalent long chain hydrocarbon group, W, is $—(CH_2)_{17}—$.

In another preferred embodiment of the invention, the divalent long chain hydrocarbon group, W, is $—(CH_2)_{18}—$.

In another preferred embodiment of the invention, the divalent long chain hydrocarbon group, W, is $—(CH_2)_{19}—$.

In another preferred embodiment of the invention, the divalent long chain hydrocarbon group, W, is $—(CH_2)_{20}—$.

In another preferred embodiment of the invention, the divalent long chain hydrocarbon group, W, is $—(CH_2)_{21}—$.

In another preferred embodiment of the invention, the divalent long chain hydrocarbon group, W, is $—(CH_2)_{22}—$.

Further preferred features of the present invention will appear from the appended claims.

Examples of preferred insulin derivatives according to the present invention are the following:

$N^{\epsilon B29}$-(CO—(CH$_2$)$_{14}$—COOH) human insulin and any zinc complexes thereof;

$N^{\epsilon B29}$-(CO—(CH$_2$)$_{16}$—COOH) human insulin and any zinc complexes thereof;

$N^{\epsilon B29}$-(CO—(CH$_2$)$_{18}$—COOH) human insulin and any zinc complexes thereof;

$N^{\epsilon B29}$-(CO—(CH$_2$)$_{20}$—COOH) human insulin and any zinc complexes thereof;

$N^{\epsilon B29}$-(CO—(CH$_2$)$_{22}$—COOH) human insulin and any zinc complexes thereof;

$N^{\epsilon B29}$-(CO—(CH$_2$)$_{14}$—COOH) ASp$^{B28}$-human insulin and any zinc complexes thereof;

$N^{\epsilon B29}$-(Co—(CH$_2$)$_{16}$—COOH) ASp$^{B28}$-human insulin and any zinc complexes thereof;

$N^{\epsilon B29}$-(Co—(CH$_2$)$_{18}$—COOH) ASp$^{B28}$-human insulin and any zinc complexes thereof;

$N^{\epsilon B29}$-(CO—(CH$_2$)$_{20}$×CooH) Asp$^{B28}$-human insulin and any zinc complexes thereof;

$N^{\epsilon B29}$-(CO—(CH$_2$)$_{22}$—COOH) Asp$^{B28}$-human insulin and any zinc complexes thereof;

$N^{\epsilon B30}$-(CO—(CH$_2$)$_{14}$—COOH) Asp$^{B28}$L -humaninsulin and any zinc complexes thereof;

$N^{\epsilon B30}$-(Co—(CH$_2$)$_{16}$—COOH) Thr$^{B29}$Lys$^{B30}$-human insulin and any zinc complexes thereof;

$N^{\epsilon B30}$-(CO—(CH$_2$)$_{18}$—COOH) Thr$^{B29}$Lys$^{B30}$-human insulin and any zinc complexes thereof;

$N^{\epsilon B30}$—(CO—(CH$_2$)$_{28}$—COOH) Thr$^{B29}$Lys$^{B30}$-human insulin and any zinc complexes thereof;

$N^{\epsilon B30}$-(CO—(CH$_2$)$_{22}$—COOH) Thr$^{B29}$Lys$^{B30}$-human insulin and any zinc complexes thereof;

$N^{\epsilon B28}$-(CO—(CH$_2$)$_{14}$—COOH) Lys$^{B28}$Pro$^{B29}$-human insulin and any zinc complexes thereof;

$N^{\epsilon B28}$-(CO—(CH$_2$)$_{16}$—COOH) LyS$^{B28}$Pro$^{B29}$-human insulin and any zinc complexes thereof;

$N^{\epsilon B28}$-(Co—(CH$_2$)$_{16}$—COOH) LyS$^{B28}$Pro$^{B29}$-human insulin and any zinc complexes thereof;

$N^{\epsilon B28}$—(CO—(CH$_2$)$_{28}$—COOH) LyS$^{B28}$Pro$^{B29}$-human insulin and any zinc complexes thereof;

$N^{\epsilon B28}$-(CO—(CH$_2$)$_{22}$—COOH) Lys$^{B28}$Pro$^{B29}$-human insulin and any zinc complexes thereof;

$N^{\epsilon B28}$—(CO—(CH$_2$)$_{22}$—COOH)Lys$^{B28}$Pro$^{B29}$-human insulin and any zinc complexes thereof;

$N^{\epsilon B29}$-(CO—(CH$_2$)$_{14}$—COOH) desB30 human insulin and any zinc complexes thereof;

$N^{\epsilon B29}$-(CO—(CH$_2$)$_{16}$—COOH) desB30 human insulin and any zinc complexes thereof;

$N^{\epsilon B29}$—(CO—(CH$_2$)$_{18}$—COOH) desB30 human insulin and any zinc complexes thereof.

$N^{\epsilon B29}$-(CO—(CH$_2$)$_{20}$—COOH) desB30 human insulin and any zinc complexes thereof; and $N^{\epsilon B29}$—(CO—(CH$_2$)$_{22}$—COOH) desB30 human insulin and any zinc complexes thereof.

DETAILED DESCRIPTION OF THE INVENTION

Terminology

The three letter codes for the amino acid residues used herein are those stated in J. Biol. Chem. 243, p. 3558 (1968).

The expression "a codable amino acid" is intended to indicate an amino acid which can be coded for by the genetic code, i.e. a triplet ("codon") of nucleotides.

Preparation of the Compounds of the Invention

The compounds of the invention can be prepared by methods known per se. Thus, the group —CO—W—COOH of formula I can be introduced into an insulin moiety via an activated ester or an activated amide, e.g. an azolide, of the diacid HOOC-W-COOH. The preparation of activated esters is described i.a. in EP 0 511 600 A2 (Kuraray Co., Ltd.) and in WO 95/07931 (Novo Nordisk A/S). The preparation of azolides is described i.a. in W. Foerst, ed. Neure Methoden Der Präparativen Organischen Chemie, Band V, p. 53–93 (Verlag Chemie, Weinheim (1967)).

The group —CO—W—COOH can be introduced into an insulin moiety in which the amino group of the N-terminal amino groups of the A-chain and the B-chain is protected. This is in analogy with the methods described in in WO 95/07931. In this case a deprotection step follows the introduction of the group —CO—W—COOH as illustrated in the appended examples 1 and 2.

Alternatively, by selecting suitable reaction conditions as described e.g. in EP 0 712 862 A2, it is possible to introduce the group —CO—W—COOH selectively into the ε-amino group of a Lys residue without resorting to protection of the N-terminal amino groups of the A-chain and the B-chain. This is illustrated in the appended examples 3 and 4.

Experimental Results Achieved with the Compounds of the Invention.

Certain experimental data on the compounds of the invention are given in Table 1.

Lipophilicity

The lipophilicity of the insulin derivatives relative to human insulin, $k''_{rel}$, was measured on a LiChrosorb RP18 (5 μm, 250×4 mm) HPLC column by isocratic elution at 40° C. using mixtures of A) 0.1 M sodium phosphate buffer, pH 7.3, containing 10% acetonitrile, and B) 50% acetonitrile in water as eluents. The elution was monitored by following the UV absorption of the eluate at 214 nm. Void time, $t_0$, was found by injecting 0.1 mM sodium nitrate. Retention time for human insulin, $t_{human}$, was adjusted to at least $2t_0$ by varying the ratio between the A and B solutions. $k'_{rel} = (t_{derivative}-t_0)/(t_{human}-t_0)$.

Determination of Disappearance Half-life, $T_50\%$, from the Injection Site after Subcutaneous Injection of an Insulin Derivative in Pigs.

$T_{50}\%$ is the time when 50% of the A14 Tyr($^{125}$I)-labeled analogue has disappeared from the site of injection as measured with an external γ-counter (Ribel, U et al., The Pig as a Model for Subcutaneous Absorption in Man. In: M. Serrano-Rios and P. J. Lefebre (Eds): Diabetes 1985; Proceedings of the 12th Congress of the International Diabetes Federation, Madrid, Spain, 1985 (Excerpta Medica, Amsterdam, (1986) 891–96).

For use in the determination of $T_{50}\%$ as described above, samples of the products to be studied were iodinated with $^{125}$I using the standard lactoperoxidase method and the Tyr$^{A14}$-labeled product was isolated by isocratic ethanol/tris HPLC.

Binding to Porcine Albumin.

The binding to porcine albumin was determined in an in vitro assay. The values given in Table 1 under the heading "Albumin binding" are relative to the reference compound EXA.

TABLE 1

| Compound[*] | Lipophilicity | $T_{50\%}$, hours | Albumin binding |
|---|---|---|---|
| EX1 | 1.4 | 5 | 0.7 |
| EX2 | 2.3 | 10 | 5 |
| EX3 | 17 | 18 | 51 |
| EX4 | 7.2 | 17.1 | 36 |
| EXA | 113 | 14 | 1 |
| EXB | 346 | 12 | 0.9 |

[*]The compounds EX1, EX2, EX3 and EX4 are the title compounds of Examples 1, 2, 3 and 4, respectively. The reference compound EXA is $N^{\epsilon B29}$-tetradecanoyl desB30 insulin and the reference compound EXB is $N^{\epsilon B29}$-hexadecanoyl desB30 insulin.

Pharmaceutical Compositions

Pharmaceutical compositions containing an insulin derivative according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the insulin derivative in the form of a nasal spray. As a still further option, it may also be possible to administer the insulin derivative transdermally.

Pharmaceutical compositions containing an insulin derivative of the present invention may be prepared by conventional techniques, e.g. as described in *Remington's Pharmaceutical Sciences*, 1985.

Thus, the injectable compositions of the insulin derivatives of the invention can be prepared using the conventional techniques of the pharmaceutical industry which involves dissolving and mixing the ingredients as appropriate to give the desired end product.

Thus, according to one procedure, the insulin derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Examples of isotonic agents are sodium chloride, mannitol and glycerol.

Examples of preservatives are phenol, m-cresol, methyl p-hydroxybenzoate and benzyl alcohol.

Examples of suitable buffers are sodium acetate and sodium phosphate.

Preferred pharmaceutical compositions of the particular insulin derivatives of the present invention are solutions of hexameric complexes. Typically, the hexameric complexes are stabilised by two or more zinc ions and three or more molecules of a phenolic compound like phenol or meta. cresol or mixtures thereof per hexamer.

In a particular embodiment, a composition is provided which contains two different insulins, one having a protracted profile of action and one having a rapid onset of action, in the form of soluble hexameric complexes. Typically the hexameric complexes are stabilized by two or more zinc ions and three or more molecules of a phenolic compound like phenol or meta-cresol or mixtures thereof per hexamer. The complexes are mixtures of hexamers of the particular insulins and mixed hexamers in which the ratio between the two different insulins is from 1:5 to 5:1.

A composition for nasal administration of an insulin derivative may, for example, be prepared as described in European Patent No. 272097 (to Novo Nordisk A/S).

The insulin derivatives of this invention can be used in the treatment of diabetes. The particular insulin derivative to be used and the optimal dose level for any patient will depend on a variety of factors including the efficacy of the specific insulin derivative employed, the age, body weight, physical activity, and diet of the patient, on a possible combination with other drugs, and on the severity of the case. It is recommended that the dosage of the insulin derivative of this invention be determined for each individual patient by those skilled in the art in a similar way as for known insulins.

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLES

The following acronyms for chemicals are used:

DMF: N,N-dimethylformamide.
DIC: N,N'-diisopropylcarbodiimide.
HOBT: 1-hydroxybenzotriazole.
TFA: trifluoroacetic acid.

Analytical

Molecular masses of the products prepared were obtained by plasma desorption mass spectrometry (PDMS) using Bio-Ion 20 instrument (Bio-Ion Nordic AB, Uppsala, Sweden).

Example 1

Synthesis of $N^{\epsilon B29}$-(CO—(CH)$_{12}$—COOH) des(B30) human insulin.

Tetradecanedioic acid (Sigma, 10 mg), HOBT (10 mg) and ethyldiisopropylamine (10 µl) was dissolved in DMF (400 µl) and DIC (6 µl) was added. The mixture was left at 25° C. for one hour and then DMF (600 µl) and A1,B1-(Boc)$_2$-des(B30) human insulin was added. After one hour at 25° C. water (200 µl) was added and after further 15 minutes precipitation of the intermediate was achieved by addition of methanol (1 ml) and ether (5 ml). The precipitate was isolated by centrifugation, washed (twice) with ether and dried. The dry intermediate was dissolved in TFA (1 ml) and after 15 minutes at 25° C. the product was precipitated by addition of ether (5 ml). The precipitate was isolated by centrifugation, washed with ether (three times) and dried.

Purification was carried out in a two-step reversed phase HPLC process on a C18 reversed phase HPLC column. First step was an isocratic run in ethanolltris-buffer (40% ethanol). The desired material, which constituted the largest peak in the chromatogram, was collected, desalted on a Sep-Pak® column, and re-chromatographed in an acetonitrile/TFA gradient (20–60% acetonitrile) with the product eluting at 45.8% acetonitrile. The purity was estimated to be >95%.

The identity of the product was confirmed by PDMS (native, reduced and digested with V8-protease) which gave MW's of 5947, 3571 and 1255 corresponding to native analogue, B-chain and the C-terminal fragment of the B-chain, respectively.

Example 2

Synthesis of $N^{\epsilon B29}$-(CO—(CH$_2$)$_{14}$—COOH) des(B30) Human Insulin.

The title compound was synthesized by proceeding as described in Example 1, except that hexadecanedioic acid was used instead of the tetradecanedioic acid.

The purification was carried out essentially as described in Example 1. In the isocratic run ethanol/tris-buffer containing 42.4% ethanol was used. The desired material, which constituted the largest peak in the chromatogram, was collected, desalted on a Sep-Pak® column, and re-chromatographed in an acetonitrile/TFA gradient (20–60% acetonitrile) with the product eluting at 48.2% acetonitrile. The purity was estimated to be >95%.

The identity of the product was confirmed by PDMS (native, reduced and digested with V8-protease) which gave MW's of 5976, 3601 and 1285 corresponding to native analogue, B-chain and the C-terminal fragment of the B-chain, respectively.

Example 3 ynthesis of $N^{\epsilon B29}$-(CO—(CH$_2$)$_{18}$—COOH) des(B30) Human Insulin.

10 mg of eicosadioic acid, 10 mg of hydroxybenzotriazole and 2.5 μl of diisopropylcarbodiimide were dissolved in 300 μl of of N-methylpyrrolidone and left at 25° C for one hour. Then, a solution of 150 mg of des(B30) human insulin in a mixture of 2 ml of water, 2.6 ml of N-methyl pyrrolidone and 200 μl of diisopropylethylamine was added and the reaction mixture was left at room temperature for one hour. The mixture was then diluted with water, applied to a C18 reversed phase HPLC column and eluted with tris buffer containing 48% of ethanol. Further purification was achieved by reversed phase HPLC on the same column by eluting with an acetonitrile/TFA gradient where the title compound eluted at 55% acetonitrile.

Example 4

Synthesis of $N^{\epsilon B29}$-(CO—(CH$_2$)$_{16}$—COOH) des(B30) Human Insulin.

Des(B30) human insulin (99 mg~17.34 μmol) was dissolved in 6 ml N-methylpyrrolidone/water (30/70 v/v) and 84 μl diisopropylethyl amine. 28.5 mg~69.4 μmol of N-(17-carboxyheptadecanoyloxy) succinimide (Mw 411) dissolved in 360 μl N-methylpyrrolidone was added. After 1 h at room temperature the reaction mixture was diluted with 6.5 ml ethanol, the pH adjusted from 11.4 to 7.3 using 1 N HCl, and the dilution subjected to anion exchange chromatography using a 1×25 cm column packed with Source™ Q15 (Pharmacia Biotech). The column was eluted at a rate of 40 ml/h using a linear gradient of KCl, from 30 mM tris pH 7.3 buffer in 50% ethanol to 200 mM KCl, 30 mM tris pH 7.3 buffer in 50% ethanol, and using 300 ml of each solvent. The title compound emerged from the column after about 200 ml of eluent, and was collected in a volume of 15 ml. The pool was diluted with 22.5 ml of water and the pH was adjusted to 6.0 using 1 N HCl. After precipitation overnight at 4° C. the product was isolated by centrifugation.

The precipitate was dissolved in 3.3 ml 20% acetonitrile (v/v) in water and the title compound was purified using 2 runs on a 1×25 cm column of dimethylbutyldimethyl substituted 5μ silica spheres, having a pore size of 100 Ångstrom. Elution was performed over 40 min at a rate of 5 ml/min, using a linear gradient from 98/2 (v/v) of solvent A: 18.75 mM (NH$_4$)$_2$SO$_4$, 12.5 mM tris pH 7.0 in 20% acetonitrile and solvent B: 80% acetonitrile, to a ratio of 40/60 (v/v) of the same solvents. The title compound emerged from the column after 21–24 min. The acetonitrile was removed by evaporation in vacuo, and the product was desalted by gel filtration using PD-10 Sephadex® G-25M in 10 mM ammoniumhydrogencarbonate/ammonia buffer pH 8.8. Finally, the product was isolated in the dry state by lyophilization. Yield 43 mg. Purity 99%.

Molecular mass of title compound found by MS: 6000±6; theory: 6003.

Example 5

Crystallization of $N^{\epsilon B29}$-(CO—(CH$_2$)$_{16}$—COOH) des(B30) Insulin in the Presence of Zinc.

Zinc containing crystals of the title compound was obtained in a tris-citrate buffer using a variety of conditions:

Insulin analogue: 7.5 mg/ml, range 2.5 to 20 mg/ml.

Zinc acetate: 1 mM.

Tris: 0.5 M

Trisodium citrate: 0.1–0.4 M.

Phenol or m-cresol: 0.05% (w/v), range 0.02–0.15% pH: 8.2.

The crystals appear as birefringent, elongated rhombohedra.

Example 6

Crystallization of $N^{\epsilon B29}$-(CO—(CH$_2$)$_{16}$—COOH) des(B30) Insulin in the Absence of Zinc.

Zinc free crystals of the title compound were obtained in sodium acetate using a variety of conditions:

Insulin analogue: 20 mg/ml, range 10 to 40 mg/ml.

Sodium acetate: 0.35–0.5 M.

Ethanol: 18%, range 15–25%.

Buffer: ammonium acetate/ammonia, 0.02 M, pH 9.0.

Phenol: optional, range 0–0.05%.

pH: 9.0

The crystals appear as non-birefringent, cubes or rhombe-dodecahedrons.

Example 7

Pharmaceutical Preparations.

A pharmaceutical solution suitable for s. c. or i. m. injection therapy may, for example, be composed as follows:

600 nmol/ml (~600 μM) of insulin analogue, e.g. of $N^{\epsilon B29}$-(CO—(CH$_2$)$_{16}$—COOH) des(B30) human insulin.

5 mM sodium phosphate buffer, pH 7.5

10 mM sodium chloride 16 mM phenol 16 mM m-cresol

200–300 μM zinc 1.6% (w/v) glycerol

What we claim is:

1. An insulin derivative having the sequence shown in Formula I:

```
                                                              Formula I
A-Chain            S─────────────S
                   │      7      │
       Gly-Ile-Val-Glu-Gln-Cys-Cys-Thr-Ser-Ile-Cys-Ser-
        1   2   3   4   5   6  │ 8   9  10  11  12
                               S
                               │
                               S
B-Chain                        │
       Xaa-Val-Xaa-Gln-His-Leu-Cys-Gly-Ser-His-Leu-Val-
        1   2   3   4   5   6   7   8   9  10  11  12
A-Chain (contd.)              20
       Leu-Tyr-Gln-Leu-Glu-Asn-Tyr-Cys-Xaa    (SEQ ID No. 1)
        13  14  15  16  17  18  19 │  21
                                   ┌─S
                                   │
                                   S
B-Chain (contd.)                   │
       Glu-Ala-Leu-Tyr-Leu-Val-Cys-Gly-Glu-Arg-Gly-Phe-
        13  14  15  16  17  18  19  20  21  22  23  24
B-Chain (contd.)
       Phe-Tyr-Thr-Xaa-Xaa-Xaa       (SEQ ID No. 2)
        25  26  27  28  29  30
``` wherein

Xaa at positions A21 and B3 are, independently, any amino acid residue which can be coded for by the genetic code except Lys, Arg and Cys;

Xaa at position B1 is deleted and the amino group of Val at position B2 has a substituent of the formula —CO—W—COOH wherein W is selected from the group consisting of —(CH$_2$)$_{16}$—, —(CH$_2$)$_{17}$—, —(CH$_2$)$_{18}$—, —(CH$_2$)$_{19}$—, —(CH$_2$)$_{20}$—, —(CH$_2$)$_{21}$— and —(CH$_2$)$_{22}$—;

Xaa at position B28 is (a) Pro, Asp or Ser in any of which cases Xaa at position B29 is Lys; or (b) Lys, in which case Xaa at position B29 is Pro; and Xaa at position B30 is deleted and any zinc complexes thereof.

2. An insulin derivative having the sequence shown in Formula I:

```
                                                              Formula I
A-Chain            S─────────────S
                   │      7      │
       Gly-Ile-Val-Glu-Gln-Cys-Cys-Thr-Ser-Ile-Cys-Ser-
        1   2   3   4   5   6  │ 8   9  10  11  12
                               S
                               │
                               S
B-Chain                        │
       Xaa-Val-Xaa-Gln-His-Leu-Cys-Gly-Ser-His-Leu-Val-
        1   2   3   4   5   6   7   8   9  10  11  12
A-Chain (contd.)              20
       Leu-Tyr-Gln-Leu-Glu-Asn-Tyr-Cys-Xaa    (SEQ ID No. 1)
        13  14  15  16  17  18  19 │  21
                                   ┌─S
                                   │
                                   S
B-Chain (contd.)                   │
       Glu-Ala-Leu-Tyr-Leu-Val-Cys-Gly-Glu-Arg-Gly-Phe-
        13  14  15  16  17  18  19  20  21  22  23  24
B-Chain (contd.)
       Phe-Tyr-Thr-Xaa-Xaa-Xaa       (SEQ ID No. 2)
        25  26  27  28  29  30
``` wherein

Xaa at positions A21 and B3 are, independently, any amino acid residue which can be coded for by the genetic code except Lys, Arg and Cys;

Xaa at position B1 is Phe, substituted in the amino group with a substituent of the formula —CO—W—COOH wherein W is selected from the group consisting of —(CH$_2$)$_{16}$—, —(CH$_2$)$_{17}$—, —(CH$_2$)$_{18}$—, —(CH$_2$)$_{19}$—, —(CH$_2$)$_{20}$—, —(CH$_2$)$_{21}$— and —(CH$_2$)$_{22}$—; and Xaa at position B28 is Lys which has a substituent in its e-amino group, of the formula —CO—W—COOH as defined above;

Xaa at position B29 is a Pro; and

Xaa at position B30 is deleted; and any zinc complexes thereof.

3. An insulin derivative having the sequence shown in Formula I:

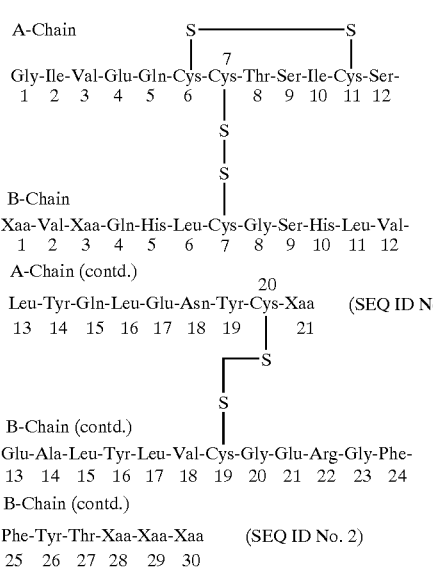

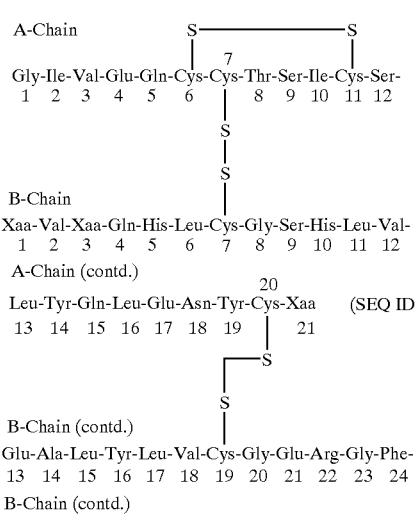

wherein

Xaa at positions A21 and B3 are, independently, any amino acid residue which can be coded for by the genetic code except Lys, Arg and Cys;

Xaa at position B1 is deleted, and the amino group of Val at position B2 has a substituent of the formula —CO—W—COOH, wherein W is selected from the group consisting of —$(CH_2)_{16}$—, —$(CH_2)_{17}$—, —$(CH_2)_{18}$—, —$(CH_2)_{19}$—, —$(CH_2)_{20}$—, —$(CH_2)_{21}$— and —$(CH_2)_{22}$—;

Xaa at position B28 is Lys having in its e-amino group a substituent of the formula —CO—W—COOH as defined above;

Xaa at position B29 is a Pro; and

Xaa at position B30 is deleted; and any zinc complexes thereof.

4. An insulin derivative having the sequence shown in Formula I:

wherein

Xaa at positions A21 and B3 are, independently, any amino acid residue which can be coded for by the genetic code except Lys, Arg and Cys;

Xaa at position B1 is deleted, and the amino group of Val at position B2 has a substituent of the formula —CO—W—COOH wherein W is selected from the group consisting of —$(CH_2)_{16}$—, —$(CH_2)_{17}$—, —$(CH_2)_{18}$—, —$(CH_2)_{19}$—, —$(CH_2)_{20}$—, —$(CH_2)_{21}$— and —$(CH_2)_{22}$—;

Xaa at position B28 is Pro, Asp or Ser;

Xaa at position B29 is Lys having in its e-amino group, a substituent of the formula —CO—W—COOH as defined above; and Xaa at position B30 is deleted; and any zinc complexes thereof.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 21 amino acids
       (B) TYPE: amino acid
       (D) TOPOLOGY: linear (ii) MOLECULE TYPE: protein (ix) FEATURE:
       (A) NAME/KEY: Variable Site
       (B) LOCATION: 21
       (D) OTHER INFORMATION: Xaa at position 21 of SEQ ID NO:1 is
          any amino acid residue which can be coded for by the
          genetic code except Lys, Arg and Cys.

(xi) SEQUENCE DESCRIPTION: SEQ ID NO:1:

Gly Ile Val Glu Gln Cys Cys Thr Ser Ile Cys Ser Leu Tyr Gln Leu
1            5                  10               15

Glu Asn Tyr Cys Xaa
          20

(2) INFORMATION FOR SEQ ID NO:2:

(i) SEQUENCE CHARACTERISTICS:
       (A) LENGTH: 30 amino acids
       (B) TYPE: amino acid
       (D) TOPOLOGY: linear (ii) MOLECULE TYPE: protein (ix) FEATURE:
       (A) NAME/KEY: Variable Site
       (B) LOCATION: 1
       (D) OTHER INFORMATION: Xaa at position 1 of SEQ ID NO:2 is
          Phe; or Phe substituted in the amino group with a
          substituent of the formula -CO-W-COOH wherein W is a
          divalent long chain hydrocarbon group having from 12 to 22
          carbon atoms; or deleted in which case the amino group of
          Val at position B2 is either unsubstituted or has a
          substituent of the formula -CO-W-COOH as defined above.

(ix) FEATURE:
       (A) NAME/KEY: Variable Site
       (B) LOCATION: 3
       (D) OTHER INFORMATION: Xaa at position 3 of SEQ ID NO:2 is any
           amino acid residue which can be coded for by the genetic
           code except Lys, Arg and Cys.

(ix) FEATURE:
       (A) NAME/KEY: Variable Site
       (B) LOCATION: 28
       (D) OTHER INFORMATION: Xaa at position 28 of SEQ ID NO:2 is
          Pro, Asp or Ser, in which case Xaa at position 29 is Lys,
          optionally substituted in the n-amino group with a
          substituent of the formula -CO-W-COOH wherein W is a
          divalent long chain hydrocarbon group having from 12 to 22
          carbon atoms, and Xaa at position 30 is Thr; or when Xaa
          at position 28 is Pro, Xaa at position 29 can be Thr and
          Xaa at position 30 can be Lys, optionally substituted in
          the n-amino group with a substituent of the formula
          -CO-W-COOH wherein W is a divalent long chain hydrocarbon
          group having from 12 to 22 carbon atoms.

(ix) FEATURE:
       (A) NAME/KEY: Variable Site
       (B) LOCATION: 29
       (D) OTHER INFORMATION: Xaa at position 29 of SEQ ID NO:2 is -continued

```
          Lys, optionally substituted in the n-amino group with a
          substituent of the formula -CO-W-COOH wherein W is a
          divalent long chain hydrocarbon group having from 12 to 22
          carbon atoms; or Pro; or Thr.

(ix) FEATURE:
       (A) NAME/KEY: Variable Site
       (B) LOCATION: 30
       (D) OTHER INFORMATION: Xaa at position 30 of SEQ ID NO:2 is
           Thr; or Lys, optionally substituted in the n-amino group
           with a substituent of the formula -CO-W-COOH wherein W is
           a divalent long chain hydrocarbon group having from 12 to
           22 carbon atoms.

(xi) SEQUENCE DESCRIPTION: SEQ ID NO:2:

Xaa Val Xaa Gln His Leu Cys Gly Ser His Leu Val Glu Ala Leu Tyr
 1           5                  10                  15

Leu Val Cys Gly Glu Arg Gly Phe Phe Tyr Thr Xaa Xaa Xaa
          20                  25                  30
```